(12) United States Patent
Plaxco et al.

(10) Patent No.: US 11,202,587 B2
(45) Date of Patent: Dec. 21, 2021

(54) DUAL-REPORTER ELECTROCHEMICAL SENSORS WITH DRIFT CORRECTION

(71) Applicant: The Regents of the University of California, Oakland, CA (US)

(72) Inventors: Kevin Plaxco, Santa Barbara, CA (US); Hui Li, Wuhan (CN); Netzahualcoyotl Arroyo Curras, Santa Barbara, CA (US); Di Kang, Glendora, CA (US); Francesco Ricci, Rome (IT)

(73) Assignee: The Regents of the University of California, Oakland, CA (US)

( * ) Notice: Subject to any disclaimer, the term of this patent is extended or adjusted under 35 U.S.C. 154(b) by 361 days.

(21) Appl. No.: 16/336,113

(22) PCT Filed: Sep. 25, 2017

(86) PCT No.: PCT/US2017/053228
§ 371 (c)(1),
(2) Date: Mar. 24, 2019

(87) PCT Pub. No.: WO2018/058028
PCT Pub. Date: Mar. 29, 2018

(65) Prior Publication Data
US 2019/0209063 A1 Jul. 11, 2019

Related U.S. Application Data

(60) Provisional application No. 62/399,480, filed on Sep. 25, 2016.

(51) Int. Cl.
*A61B 5/145* (2006.01)
*A61B 5/1473* (2006.01)
(Continued)

(52) U.S. Cl.
CPC ........ *A61B 5/14546* (2013.01); *A61B 5/0031* (2013.01); *A61B 5/1473* (2013.01);
(Continued)

(58) Field of Classification Search
CPC ....... A61B 5/1456; A61B 5/24; A61B 5/0031; A61B 5/1473; C12Q 1/6825;
(Continued)

(56) References Cited

U.S. PATENT DOCUMENTS

2007/0270675 A1 11/2007 Kane et al.
2014/0012118 A1 1/2014 Mensinger et al.
(Continued)

FOREIGN PATENT DOCUMENTS

KR 10-2015-0020629 A 2/2015
WO 2014/143427 A1 9/2014

OTHER PUBLICATIONS

Li, Hui, et al. "Dual-reporter drift correction to enhance the performance of electrochemical aptamer-based sensors in whole blood." Journal of the American Chemical Society 138.49 (2016): 15809-15812. (Year: 2016).*

(Continued)

*Primary Examiner* — Robert J Eom (57) ABSTRACT

The invention encompasses novel methods of operating electrochemical sensors such as aptamer-based sensors to analyze complex samples, such as flowing whole blood both in vitro or in vivo. In such environments, electrochemical sensors are often subject to drift, which complicates the interpretation of sensor output in terms of target concentration. The method of the invention utilizes a dual-reporter recognition element that generates a first, sensing current that is responsive to target binding and to environmental factors and a second, reference current that is only affected by environmental factors. The reference current provides (Continued)

information about environmentally-induced drift, which allows the drift effect to be subtracted out. By removing drift artifacts, electrochemical sensors may be deployed to analyze complex samples, such as whole blood, in vivo.

9 Claims, 9 Drawing Sheets

(51) Int. Cl.
| | | |
|---|---|---|
| *C12Q 1/6825* | (2018.01) | |
| *G01N 27/327* | (2006.01) | |
| *G01N 33/543* | (2006.01) | |
| *G01N 33/542* | (2006.01) | |
| *A61B 5/24* | (2021.01) | |
| *A61B 5/00* | (2006.01) | |

(52) U.S. Cl.
CPC .............. *A61B 5/24* (2021.01); *C12Q 1/6825* (2013.01); *G01N 27/3275* (2013.01); *G01N 33/542* (2013.01); *G01N 33/5438* (2013.01); *G01N 33/54353* (2013.01)

(58) Field of Classification Search
CPC .............. G01N 27/3275; G01N 33/542; G01N 33/54353; G01N 33/5438
See application file for complete search history.

(56) References Cited

U.S. PATENT DOCUMENTS

| | | |
|---|---|---|
| 2014/0278189 A1 | 9/2014 | Vanslyke et al. |
| 2016/0113587 A1 | 4/2016 | Kothe et al. |

OTHER PUBLICATIONS

Lauren R. Schoukroun-Barnes et al, "Heterogeneous Electrochemical Aptamer-Based Sensor Surfaces for Controlled Sensor Response". Langmuir, vol. 31. No. 23. Jun. 2, 2015 (Jun. 2, 2015). pp. 6563-6569. XP055687128, US ISSN: 0743-7463. DOI: 10.1021jacs.langmuir.5b01418, the whole document.
Corresponding European Search Report, Appln No. EP 17854067, dated Apr. 30, 2020.

* cited by examiner

DUAL-REPORTER ELECTROCHEMICAL SENSORS WITH DRIFT CORRECTION

CROSS-REFERENCE TO RELATED APPLICATIONS

This application claims priority to International Application No. PCT/US2017/053228, entitled "Dual-reporter Electrochemical Sensors with Drift Correction," filed on Sep. 25, 2017, which claims priority to U.S. Provisional Application No. 62/399,480, entitled "Dual-Label Electrochemical Sensors with Drift Correction," filed on Sep. 25, 2016, each of which is incorporated by reference herein in its entirety.

STATEMENT REGARDING FEDERALLY SPONSORED RESEARCH OR DEVELOPMENT

This invention was made with government support under grant number W911NF-09-D-0001 awarded by the Army Research Laboratory. The government has certain rights in the invention.

BACKGROUND OF THE INVENTION

The continuous, real-time monitoring of drugs, metabolites, hormones and other specific molecular targets in vivo or in unprocessed clinical samples would enable many transformative medical applications. Electrochemical aptamer-based (E-AB) sensors are a promising platform because of their good selectivity, reversibility and reagentless features. E-AB sensors are comprised of an electrode-bound, redox reporter-modified aptamer that undergoes a conformational change upon target binding. This conformational change alters the accessibility of the reporter relative to the electrode, producing a target-induced change in current between the redox reporter and the electrode. This signal transduction mechanism is rapid, reagentless, and reversible, and supports continuous monitoring at fine time scales.

An issue that hinders the accuracy of E-AB sensors is the baseline signal drift that is observed when these sensors are operated in complex samples, such as in whole blood. Signal may drift by 10-30% per hour, which seriously complicates the interpretation of sensor outputs. The source of signal drift is not well understood, but it is presumably due to random non-specific interactions between the recognition elements of the sensor and proteins or other species present in the sample, which interfere with redox reporter signaling. In the case of whole blood, the formation of macroscopic aggregates of blood cells on the sensor surface is a likely contributor to signal drift.

A different problem associated with E-AB sensors is that they can suffer from inconsistencies in manufacturing that result in significant variations in the number of redox reporters per sensor. These include differences in surface area, differences in the number of aptamers packed per unit area, and differences in the efficiency with which the aptamer is modified with the redox reporter. This variability means that even under identical operating conditions, individual sensors will have different baseline currents. One approach to solving this problem is rigorous fabrication approaches that accurately control all of the relevant variables. Alternatively, Ellington et al. (Ellington, A. D. *Anal. Chem.* 2014, 86, 8010) addressed this issue by the development of a dual-reporter sensor that can correct for variability in sensor-to-sensor fabrication. The Ellington sensor's recognition element has two redox reporters, a first sensing reporter in the typical E-AB redox reporter configuration that creates a current responsive to target binding. The Ellington sensor further comprises a second redox reporter that is insensitive to target binding. The current output by the second redox reporter is proportional to the number of recognition elements present on the sensor, and thus, sensor-to-sensor variability in recognition element abundance can be normalized by ratiometric comparison between the sensing current to the reference current. That is, by taking the ratio of the two signals, the sensor output is corrected for any variations in fabrication.

The Ellington ratiometric approach corrects for sensor-to-sensor variability, however, it does not eliminate signal drift. Accordingly, there remains a need in the art for methods to prevent or correct for signal drift in E-AB sensors caused by the species prevalent in complex samples.

SUMMARY OF THE INVENTION

Building on the dual-reporter sensor concept, the inventors of the present disclosure have developed novel methods of correcting for signal drift in E-AB sensors. The methods of the invention are based on the use of a second redox reporter that is insensitive to target binding, employing the second redox reporter in a differential, rather than a ratiometric fashion.

The inventions disclosed herein provide the art with a means of operating E-AB sensors in complex samples. This greatly expands the ability to deploy sensors for point-of-care applications with unprocessed samples, in vivo uses, and other contexts. Furthermore, the concepts demonstrated herein for E-AB sensors may be extended to other electrochemical sensing platforms.

BRIEF DESCRIPTION OF THE DRAWINGS

FIGS. 1A and 1B. FIG. 1A depicts a dual-reporter sensor comprising an electrode substrate (101) to which an aptamer (102) is bound. The aptamer is functionalized with a sensing redox reporter (105), in this case methylene blue (MB), in a position that moves towards or (less typically) away from the electrode upon target binding. The aptamer is also functionalized with a reference redox reporter (103), in this case anthraquinone (AQ), in a position proximal to the electrode and that is unaffected by target binding. The proximity of the AQ reporter to the electrode results in ready electron transfer (eT, 104). In FIG. 1A, target is not bound to the aptamer and the sensing reporter (105) is free to move away from the electrode substrate, such that electron flow from the redox reporter to the electrode is minimal. FIG. 1B depicts the signal-on dual-reporter sensor, wherein a target molecule (106) has bound to the aptamer (102), changing its conformation such that the sensing reporter (105) is held in proximity to the electrode (101), facilitating electron transfer (eT, 107) from the sensing redox reporter to the electrode (101). Electron flow (104) from the reference redox reporter, in contrast, (103) is unaffected by target binding.

FIGS. 2A, 2B, 2C, and 2D. FIG. 2A shows sensor current output in buffer with peaks for methylene blue (MB) and anthraquinone (AQ), at different target concentrations (0, 0.1, and 1.0 mM), wherein the MB current responds significantly to target concentration while the AQ signal is nearly insensitive to the sensor's target. FIG. 2B depicts the voltammogram when the sensor is placed in flowing, undiluted whole blood with no target present, showing significant signal drift over time. Because the signals drift in concert, taking the difference between their normalized currents ("Difference") affords excellent drift correction. Here normalized means the signal observed in the sample divided by the signal observed in a matched sample of known target concentration, such as one lacking target (zero target concentration). FIG. 2C depicts the voltammogram when the sensor is placed in flowing, undiluted whole blood with different concentrations of target present, where both signals drift and the MB current responds to changes in target concentration. FIG. 2D depicts the difference between normalized currents in FIG. 2C.

FIGS. 3A, 3B, 3C, and 3D. FIG. 3A shows current output in buffer, with peaks for methylene blue (MB) and anthraquinone (AQ), at different target concentrations (0, 0.16, and 1.6 mM), wherein the MB current responds significantly to target concentration while the AQ signal is insensitive to the sensor's target. FIG. 3B depicts the voltammogram when the sensor is placed in flowing, undiluted whole blood with no target present, showing significant signal drift over time. Because the signals drift in concert, taking the difference between their normalized currents (Difference) affords excellent drift correction. FIG. 3C depicts the voltammogram when the sensor is placed in flowing, undiluted whole blood with different concentrations of target present, where both signals drift and the MB current responds to changes in target concentration. FIG. 3D depicts the difference between normalized currents in FIG. 3C.

FIGS. 4A, 4B, and 4C.

DETAILED DESCRIPTION OF THE INVENTION

The scope of the invention encompasses methods of using dual-reporter electrochemical sensors to address the problem of baseline signal drift when such sensors are deployed in complex samples such as unprocessed clinical samples or flowing whole blood. The methods of the invention encompass the use of electrochemical sensors wherein the sensor's recognition elements are modified with two redox reporters, one of which that responds to the presence of the target and a second redox reporter that responds to environmental effects but that is insensitive to the presence or absence of target. The second redox reporter thus serves as a reference that can be used to correct for the background environmental effects on sensing current, thus improving measurement accuracy and stability.

Dual Reporter Electrochemical Sensors. The methods of the invention are directed to electrochemical sensors configured to detect a target species. These electrochemical sensors comprise a sensing element. The basic components of the sensing element are:
 a working electrode;
 a plurality of recognition elements attached to the electrode;
  wherein each recognition element is capable of selectively binding a target species;
  wherein each recognition element is functionalized with a first, sensing redox reporter, wherein binding of the target species to the recognition element causes a detectable change in electron transfer between the sensing redox reporter and the electrode;
  wherein each recognition element is functionalized with a second, reference redox reporter, wherein binding of the target species to the recognition element does not affect electron transfer between the reference redox reporter and the electrode.

The sensing elements of the invention may be incorporated into sensor assemblies or sensor systems for the detection of target species by various electrochemical interrogation techniques. The various elements of the invention are next described in detail.

Targets. The sensing elements of the invention are directed to the detection of a target species. The target species may comprise any inorganic or organic molecule, for example: a small molecule drug, a metabolite, a hormone, a peptide, a protein, a carbohydrate, a nucleic acid, a lipid, a hormone, a metabolite, a growth factor, a neurotransmitter, a nutrient, a pollutant, a pathogen-induced or pathogen-derived factor, or any other composition of matter. In addition to molecules, the target species may comprise large and complex targets such as a cell.

Electrodes. The sensing elements of the invention will comprise one or more working electrodes to which a plurality of recognition elements is bound. The one or more electrodes may comprise various materials and configurations. The electrode may comprise any suitable electrode material for electrochemical sensing, including, for example: gold or any gold-coated metal or material, titanium, tungsten, platinum, carbon, aluminum, copper, palladium, mercury films, silver, oxide-coated metals, semiconductors, graphite, carbon nanotubes, and any other conductive material upon which biomolecules can be conjugated.

The electrode may be configured in any desired shape or size, including discs, strips, rectangular electrodes, electrode arrays, wires, and other configurations.

Recognition Elements. In an E-AB sensor, the recognition element comprises an aptamer, as known in the art. The aptamer may comprise a DNA aptamer, RNA aptamer, or an aptamer comprising non-natural nucleic acids, as well as hybrids of the foregoing. Variants of the E-AB concept wherein the recognition element is a nucleic acid other than an aptamer, or is other than a nucleic acid, for example sensors using proteins or fragments thereof, are also within the scope of the invention.

Anchoring Chemistry. The recognition elements are bound to the surface of the electrode. The recognition element may be conjugated to or otherwise associated with the electrode surface by any appropriate chemistry, for example by covalent bonding to the electrode or to a monolayer on the electrode, or via chemisorption or adsorption. Alkane thiol monolayers may be used to conjugate aptamers to the electrode surface. The anchoring moiety may comprise a species that is capable of directly conjugating to the electrode surface. Alternatively, the anchoring species may be capable of conjugation to a complementary functional group with which the electrode surface has been modified or decorated. Anchoring moieties may comprise elements that form self-assembled monolayers on the electrode surface. The recognition elements may be deposited on the electrode surface at any desired density, for example, in the range of $1\times10^9$ to $1\times10^{12}$ molecules/cm$^2$.

Redox Reporters. Redox reporters are chemical entities capable of electron transfer to or from the electrode in response to an excitation stimulus, for example, a potential step applied to the working electrode in a voltammetric scan. With sufficient proximity and accessibility of a redox reporter to the electrode, an electrical signal, e.g. current, voltage, or other measurable electrical interaction, will occur between the redox reporter and the electrode upon excitation of the electrode. In the sensors of the invention, the recognition elements of the sensor are functionalized with at least two different redox reporters.

The first redox reporter, which is referred to herein as the "sensing reporter," is positioned on the recognition element as in conventional electrochemical sensors, wherein binding of the target species to the recognition element causes conformational change in the recognition element which changes the accessibility of the sensing redox reporter with respect to the electrode. Alternatively, in some implementations, steric-interference effects from target binding cause measurable change in the electrical signal generated by the sensing reporter. In another implementation binding causes the sensing reporter to be excluded from a pocket on the recognition element, improving its electron transfer abilities. Recognition elements may be configured for turn-off sensing, turn-on sensing, or strand displacement sensing, as known in the art. The placement of such sensing reporter can be at the 5' end, 3' end, or otherwise engineered using known methods. The current flowing between the sensing reporter and the electrode will be referred to herein as the "sensing current."

The second redox reporter, which is referred to herein as the "reference redox reporter," is positioned on the recognition element such that conformational changes in the recognition element caused by target binding do not significantly affect the relative position or accessibility of the reference reporter with respect to the electrode. At the same time, the reference reporter is positioned such that it is subject to the same non-specific interactions with the sample environment that affect the electrical interactions between the electrode and the sensing reporter. The current flowing between the reference redox reporter and the electrode will be referred to herein as the "reference current."

In one embodiment, the reference reporter is placed within the proximal (nearest to the electrode) portion of the recognition element. For example, the reference reporter may be placed between the anchoring moiety and the proximal end of the recognition element. For example, in one embodiment, the reference redox reporter is disposed between the distal (further from the electrode) end of a thiolated alkyl chain and the 5' end of an aptamer. Spacers or linkers may be placed between the reference reporter and the anchoring moiety and/or the recognition element to optimize its sensing of non-specific interactions with the sample microenvironment and/or minimize changes in its interactions with the electrode caused by binding of the target species to the recognition element.

The selection of the two redox species used for the sensing and reference reporters is based on the following guidelines. The two redox species must interact with the selected electrode material and electrode configuration such that both produce a measurable signal and such that the two signals are distinct. For example, the redox potentials of both reporter species may be in the range from –0.4 V to 0.3 V (versus an Ag/AgCl reference electrode), and can optimally be distinguished form each other where their redox potentials are at least 0.2 V apart from each other. Additionally, both reporter species should behave similarly in terms of electron transfer rates. Lastly, both reporters should have similar chemical and electrochemical stability.

Exemplary redox species include methylene blue, ferrocene, viologen, anthraquinone or any other quinones, daunomycin, organo-metallic redox reporters, for example porphyrin complexes or crown ether cycles or linear ethers, ruthenium, bis-pyridine, tris-pyridine, bis-imidizole, cytochrome c, plastocyanin, and ethylenetetracetic acid. Exemplary redox reporter pairs include methylene blue and anthraquinone, methylene blue and ferrocene, and anthraquinone and ferrocene.

For convenience, this description of the invention is directed to recognition and signaling constructs comprising two separate redox reporters. It will be understood that the scope of the invention extends to recognition and signaling constructs that comprise three or more separate redox reporter reporters, wherein multiple sensing and/or reference reporters are present, generating additional data for interpreting signals and formulating correction factors.

Sensor Fabrication. The sensors of the invention may be fabricated based on methods of fabricating E-AB sensors, as known in the art. For example, sensors may be prepared as described in: Xiao, Y., Rowe, A. A., and Plaxco, K. W. (2007) Electrochemical detection of parts per billion lead via an electrode-bound DNAzyme assembly. *J. Am. Chem. Soc.* 129, 262-263; U.S. Pat. No. 8,003,374 by Heeger, Fan, and Plaxco; Ferguson et al., "Real-time, aptamer-based tracking of circulating therapeutic agents in living animals," *Sci Transl Med.* 2013 Nov. 27; 5(213): 213ra165; and Swensen et al., "Continuous, Real-Time Monitoring of Cocaine in Undiluted Blood Serum via a Microfluidic, Electrochemical Aptamer-Based Sensor," *J Am Chem Soc.* 2009 Apr. 1; 131(12): 4262-4266.

Sensor Assemblies. The electrochemical sensing elements of the invention may be configured in various assemblies to make fully functional sensing systems. As used herein, a sensor assembly will comprise a collection of elements that may operate together to perform various operations of the sensing process. For example, in one embodiment, the invention comprises a sensor assembly comprising a sensing element and a reference electrode, for example an Ag/AgCl electrode, or other reference electrode known in the art. The sensing assemblies of the invention may further comprise an auxiliary or counter electrode, for example, a platinum auxiliary electrode. The sensor assemblies of the invention may be configured in a three-electrode cell system comprising one or more sensing, reference, and auxiliary electrodes, appropriately configured for performing electrochemical interrogation measurements. The three-electrode cell system may comprise a mixing chamber or other vessel wherein the electrodes are present and are contacted with the sample.

In some embodiments, the sensor assembly comprises a tabletop lab apparatus. In other embodiments, the sensor assembly comprises a hand-held device. In other embodiments, the sensor assembly comprises a microfluidic biochip. In one embodiment, the sensor assembly of the invention is configured as an in vivo sensor, configured to sample fluids within the body of a living organism wherein the sensing element is inserted, implanted, or otherwise placed within the body of a living organism. For in vivo measurements, a sensing assembly comprising a thin wire configuration is advantageous, as the low-profile wire may be inserted into veins, arteries, tissue or organs and will minimally impede blood flow in blood vessels or will cause minimal damage in the sampled area. For example, a wire having a diameter of 1-500 μm, for example, 100 μm, may be used. In one embodiment, the sensing assemblies are housed in a needle, catheter, or cannula that may be inserted into a vein, blood vessel, organ, tissue, or interstitial space in order to place the sensor in the target environment. The needle, catheter, or cannula may be porous, comprising a plurality of holes or channels distal to the tip in order to allow the flow of blood over the sensor assembly.

The sensors of the invention may also be used in ex vivo applications. In one embodiment, a sample is withdrawn from a living organism and the concentration of the target species in the sample by the methods of the invention. In one embodiment, the sensors of the invention are employed in point-of-care testing systems. In one embodiment, the sample is a blood sample, for example, a self-withdrawn pin-prick or finger-prick blood sample, or a urine, sweat, or saliva sample.

The sensor assemblies of the invention may further comprise or be in connection with appropriate electronic components for performing electrochemical measurements. The electronic components may comprise two or more devices in electrical and/or network connection with one another, or may comprise a single integrated device.

Electronic components may include potientiostats or other voltage sources and voltage controllers. The system may further comprise appropriate circuitry for reading sensor outputs, and storing such outputs or routing the outputs to other devices. The systems of the invention may further comprise data processing means, for example, a general-purpose computer or other data processor capable of carrying out the various calculations utilized in the methods of the invention. The scope of the invention further encompasses non-transitory computer-readable recording media having stored thereon an encoding program that causes a computer to execute a process, the process comprising one or more data processing calculations for readout and interpretation of signals from a sensing element.

Alternative Sensor Designs. For convenience, the description of the invention is directed to EA-B sensor configurations. However, it will be understood that the scope of the invention extends to other electrochemical sensor types wherein a conformational change in the recognition element induced by target binding alters the electron flow between a redox reporter and an electrode substrate. For example, the methods of the invention may be applied to various sensors such as DNA-based electrochemical "switches," wherein the recognition element comprises a modified DNA stem loop, as described in Vallee-Balisle et al., Bio-electrochemical switches for the quantitative detection of antibodies directly in whole blood, J Am Chem Soc, 2012 Sep. 19; 134. Another exemplary sensor type amenable to the methods of the invention are aptamer duplex sensors, wherein the complementary strand keeps a redox reporter in position away from the electrode and is displaced by target binding, making the redox reporter more accessible to the electrode substrate, as described in Zuo et al., A Target-Responsive Electrochemical Aptamer Switch (TREAS) for Reagentless Detection of Nanomolar ATP, J Am Chem Soc 2007 129, 5 pp 1042-2043.

Methods. The scope of the invention encompasses methods of measuring the concentration of the target species in a sample by the use of a dual-reporter electrochemical sensor, wherein drift effects in the sensing signal are corrected for by use of the reference signal.

Measurement is carried out by exposing the sensing element to a sample. The sample may comprise a liquid. The sample may comprise whole blood, serum, saliva, urine, sweat, interstitial fluid, spinal fluid, cerebral fluid, tissue exudates, macerated tissue samples, cell solutions, intracellular compartments, water, food, groundwater, or other biological and environmental samples. In some embodiments, the sample is derived from a subject, for example a human patient or a non-human animal such as a veterinary subject or test animal. In one embodiment, the sample comprises flowing whole blood, e.g., in the circulatory system of a subject. In an alternative embodiment, the sample is a gas. In some embodiments, the sample has been processed prior to performing measurements. Examples of processing include filtering, dilution, buffering and the application of other materials or processes to the sample prior to analysis.

Measurement is made over a selected time interval when the sensing element of the electrochemical sensor is contacted with the sample. Measurements over the time interval are made by voltammetric interrogation of the electrode to assess sensing and reference currents. Interrogation can be by any voltammetric method, including cyclic voltammetry, differential pulse voltammetry, alternating current voltammetry, square wave voltammetry, potentiometry or amperometry, as known in the art. Waveforms may be selected as known in the art. Each scan will be performed across a range of voltages which results in distinct signals being generated from the sensing redox reporter and reference redox reporter. Scans can be performed at discreet time intervals or continuously over the measurement period. In one embodiment, peak currents for the two redox reporters are selected as the representative signal values.

Drift Correction. Sensing signal will be expected to drift over time, especially in complex samples. Because the sensing signal and reference signal drift in parallel, the drift effect can be subtracted out to yield a corrected signal value that is attributable to target binding. The general method of the invention therefore comprises a method of measuring the concentration of a target species in a sample by the use of a dual-reporter electrochemical sensor which outputs a sensing signal and a reference signal, wherein the drift component of the sensing signal is quantified by the use of the reference signal, and is removed.

In a first implementation, the method comprises the calculation a normalized drift-corrected signal by the use of a dual-reporter electrochemical sensor, by the steps of:

exposing the dual-reporter sensor to a calibration sample of known target concentration and measuring both the sensing signal and the reference signal ("baseline signals");

exposing the dual-reporter sensor to a sample of unknown target concentration and measuring both sensing signal and reference signal in the sample of unknown target concentration;

calculating the normalized sensing signal, which is the ratio between sensing signal measured in the sample of unknown target concentration and the baseline sensing signal;

calculating the normalized reference signal, which is the ratio between reference signal measured in the sample of unknown target concentration and the baseline reference signal;

subtracting the normalized reference signal, which is indicative of drift, from the normalized sensing signal, which is indicative of both drift and target binding;

wherein the difference comprises a drift-corrected normalized signal responsive only to target induced binding.

The baseline calibration sample is a sample of known target concentration. In one implementation, it may comprise a sample with zero target, or in alternative implementation it could be a reference sample containing target of known concentration. For example, the calibration standard may be selected as the first data point collected in the assay if the sample stream is known to lack target at this time.

It will be understood that the order of the first and second steps is not critical to the method, and baseline signals may be collected after measurement of signals in the sample of unknown target concentration. It will be understood that the first sample of known concentration and second sample of unknown concentration may comprise the same sample at different time points, for example, a sample that is undergoing dynamic changes in target concentration, for example as in an in vivo sensor.

In one embodiment, the corrected drift-corrected normalized signal is determined as:

$$S_{cor} = \frac{i_S}{i_{S0}} - \frac{i_R}{i_{R0}} \qquad \text{[Equation 1]}$$

wherein $S_{cor}$ is the drift-corrected normalized signal, $i_S$ and $i_R$ are, respectively, the sensing current and reference current measured in the sample of unknown concentration, and $i_{S0}$ and $i_{R0}$ are, respectively, the baseline sensing and reference currents measured when the sensor was exposed to the calibration sample, i.e. a sample lacking the target or containing an otherwise known target concentration.

Figure 4A:
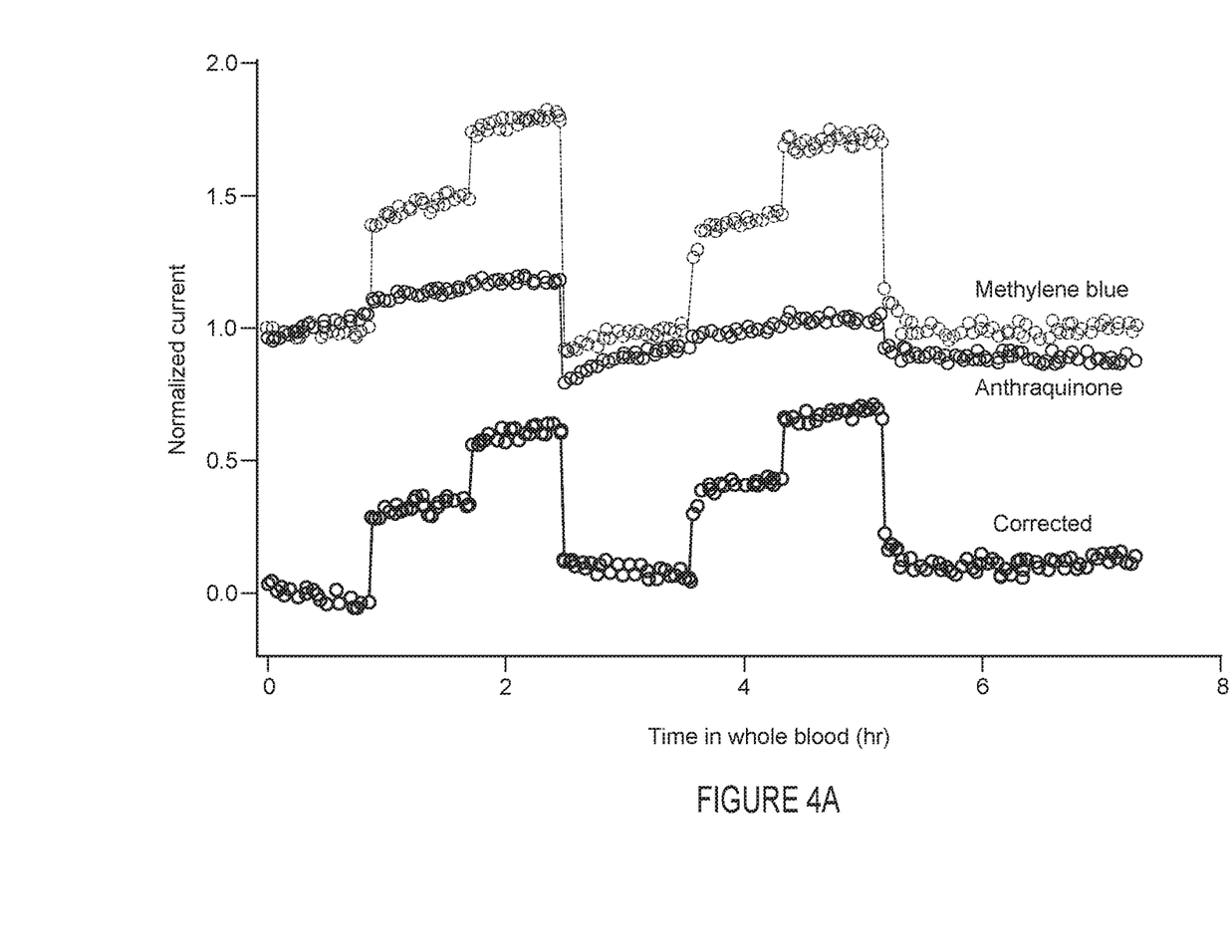
FIG. 4A depicts normalized MB and AQ currents for a cocaine sensing aptamer-based dual reporter sensor.
Figure 4B:
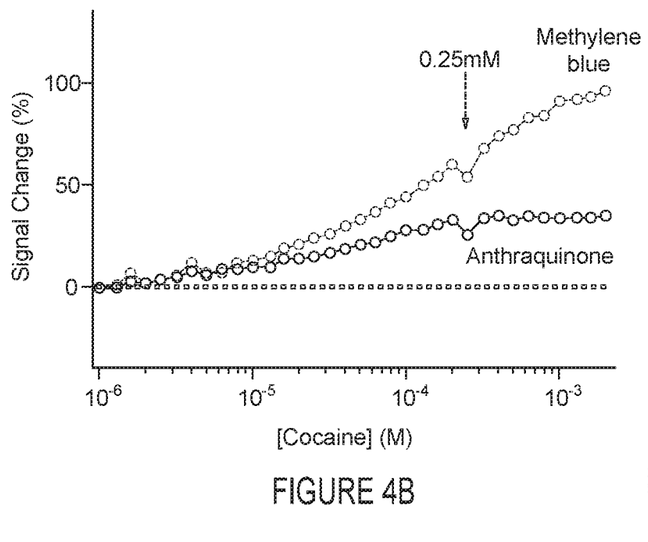
FIG. 4B depicts the dose response of change in normalized MB and AQ signals to different cocaine concentrations.
Figure 4C:
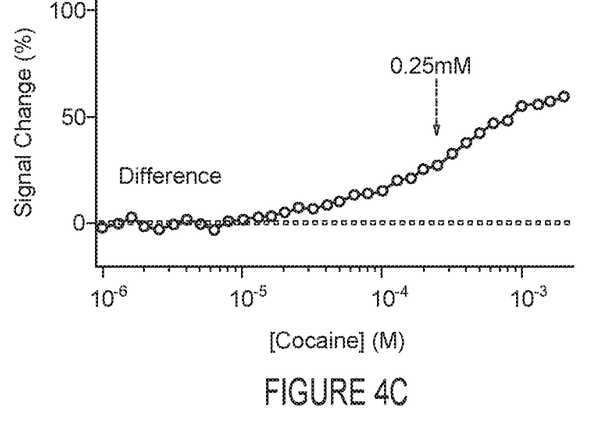
FIG. 4C depicts the drift-corrected signal change over a range of cocaine concentrations, being the difference between the normalized MB and AQ currents in FIG. 4B.

In a further step, the drift-corrected change in signal can be converted to a target concentration value by comparing it against a standard curve, applying a conversion factor, or performing any other step that relates the drift-corrected normalized signal to target concentration. For example, a drift-corrected normalized signal versus concentration plot as in FIG. 4C may be employed to relate normalized signals to target concentrations.

For example, in one embodiment, a calibration curve is generated by exposing a sensor to a first calibration sample, for example, zero target, and then exposing the sensor to a series of calibration standards of different target concentration, and monitoring sensing and reference currents. Normalized sensing and reference currents (vs. baseline current in the calibration sample, for example using target concentration of zero as the calibration standard for normalization) are then calculated (as in FIG. 4B). Drift corrected signal change can then be calculated by subtracting normalized reference current from normalized sensing current, (as in FIG. 4C).

In one embodiment, to determine target concentration for a given drift-corrected measurement, the calibration curve derived as described above can be fit to a Langmuir isotherm model, or like equation, as in Equation 2

$$S_{cor}(\%) = \frac{a[T]}{K_D + [T]}. \qquad \text{Equation 2}$$

wherein $S_{cor}$ is the drift-corrected normalized signal, [T] is the target concentration, a is constant, and $K_D$ is dissociation constant. Fitting of the curve enables calculation of a and $K_D$. Rearranging, by Equation 3, $S_{cor}$ values can be converted to target concentration values:

$$[T] = S_{corr} * \frac{K_D}{a - S_{cor}}. \qquad \text{Equation 3}$$

wherein $S_{cor}$ is the drift-corrected normalized signal, [T] is the target concentration, a is the previously calculated constant, and $K_D$ is the previously calculated dissociation constant, enabling measured $S_{cor}$ values to be converted to target concentration values.

EXAMPLES

Example 1

Dual-Reporter Electrochemical Sensors with Drift Correction

Figure 1A:
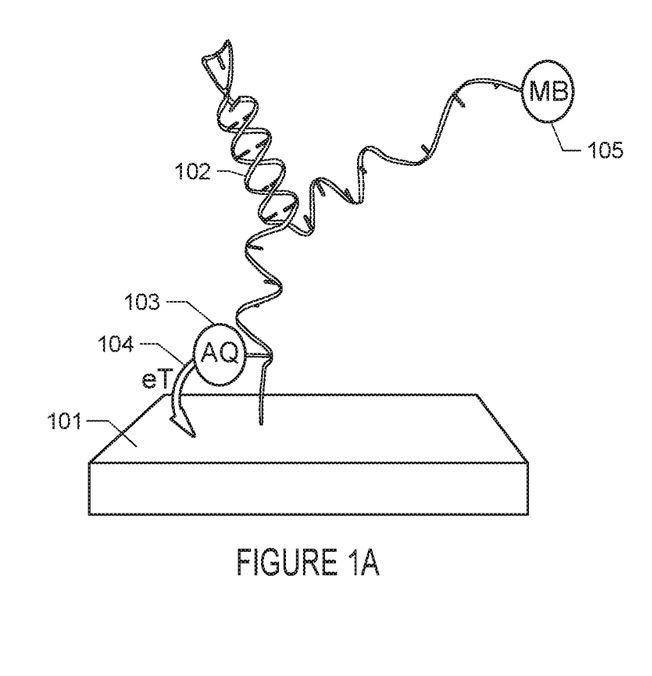
FIGS. 1A and 1B depict a signal-on dual-reporter aptamer-based sensor as utilized in the methods of the invention.
Figure 1B:
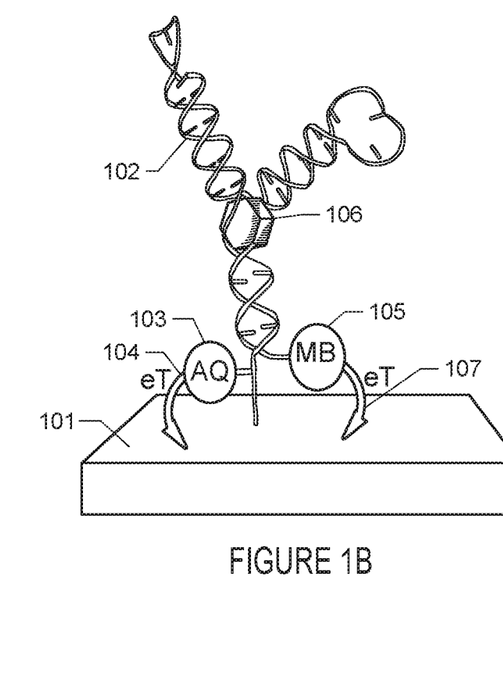
Figure 2A:
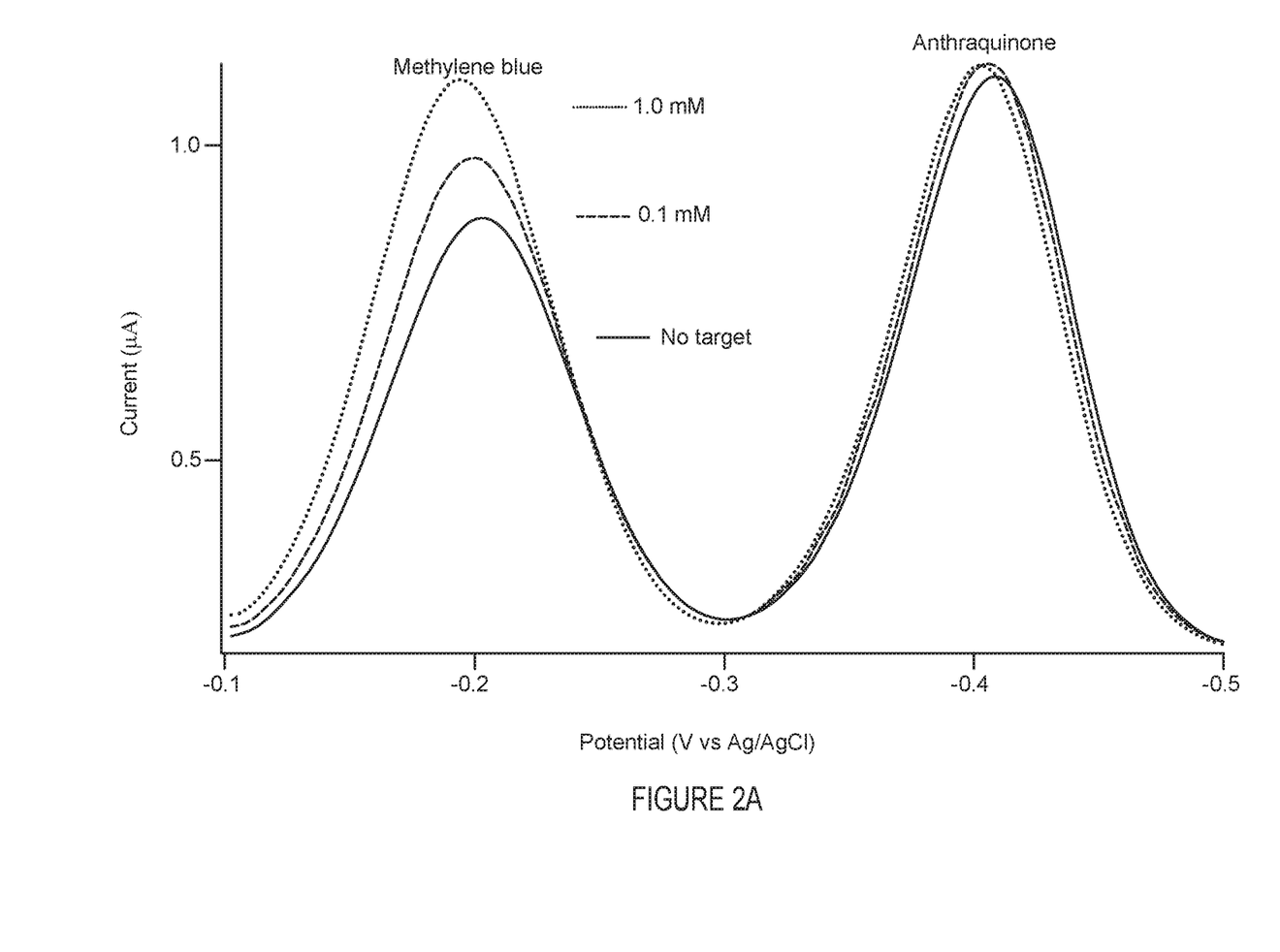
FIGS. 2A, 2B, 2C, and 2D depict voltammograms averaged for four dual-reporter cocaine-detecting E-AB sensors.

E-AB sensors were fabricated with a cocaine-binding aptamer as the recognition element, modified on its distal end with a sensing redox reporter comprising methylene blue (MB) and modified on its proximal (near-electrode) end with a reference redox reporter comprising anthraquinone (AQ). Using square wave voltammetry to interrogate the sensors in phosphate-buffered saline (PBS) the expected redox peaks at −0.26 V and −0.48 V were observed, corresponding to the reduction of MB and AQ respectively (FIG. 2A). As expected, the current originating from the MB reporter increased significantly and monotonically upon spiking the system with increasing concentrations of cocaine. The current from the AQ reporter, in contrast, was largely insensitive to the presence of the target, demonstrating that it would serve as a suitable drift-correction reference.

Figure 2B:
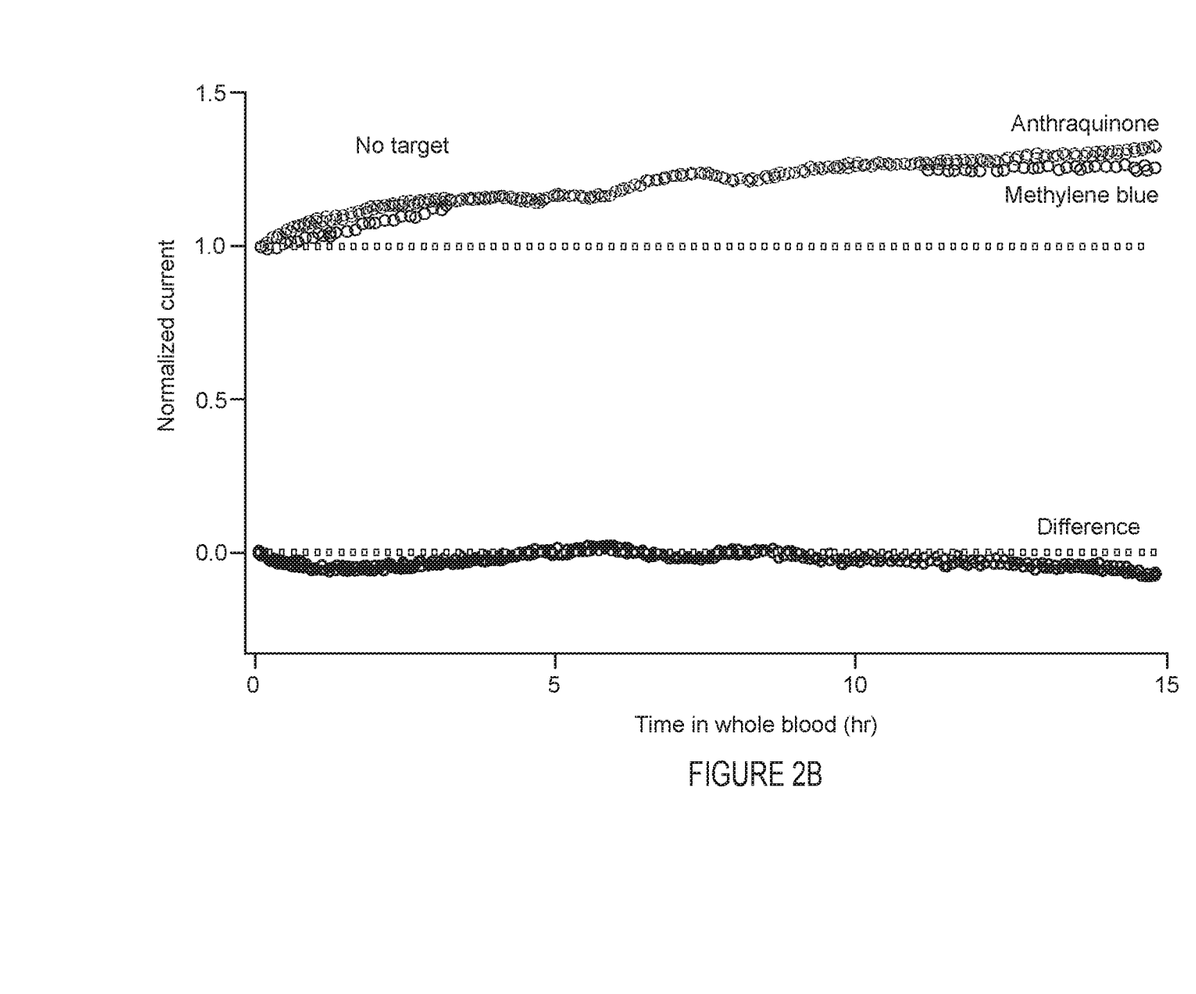

To test the ability of the AQ reporter to provide stable drift correction, a set of sensors was challenged in flowing, undiluted whole blood using an in-vitro system meant to mimic circulation in the vasculature. Under these conditions, the currents of both MB and AQ drift by 20%-30% over the course of 15 hours (averaged over multiple sensors). The two currents drift in concert (FIG. 2B).

The reference current was normalized and then used to correct the normalized sensing current by application of the following equation:

$$S_{cor} = \frac{i_{MB}}{i_{MB0}} - \frac{i_{AQ}}{i_{AQ0}} \qquad \text{Equation 4}$$

in which $S_{cor}$ is the corrected normalized signal change, $i_{MB}$ and $i_{AQ}$ are the currents from the MB and AQ, respectively, and $i_{MB0}$ and $i_{AQ0}$ are the currents collected as the first data point in each experiment. Using this approach, the drift effect was reduced to less than 2% after 15 hours in flowing whole blood. And while the drift observed for individual sensors often varies dramatically (presumably due to the formation of macroscopic—and thus somewhat stochastic-aggregates of blood cells on the sensor surface), the drift correction itself is quite reproducible from one sensor to the next.

Figure 2C:
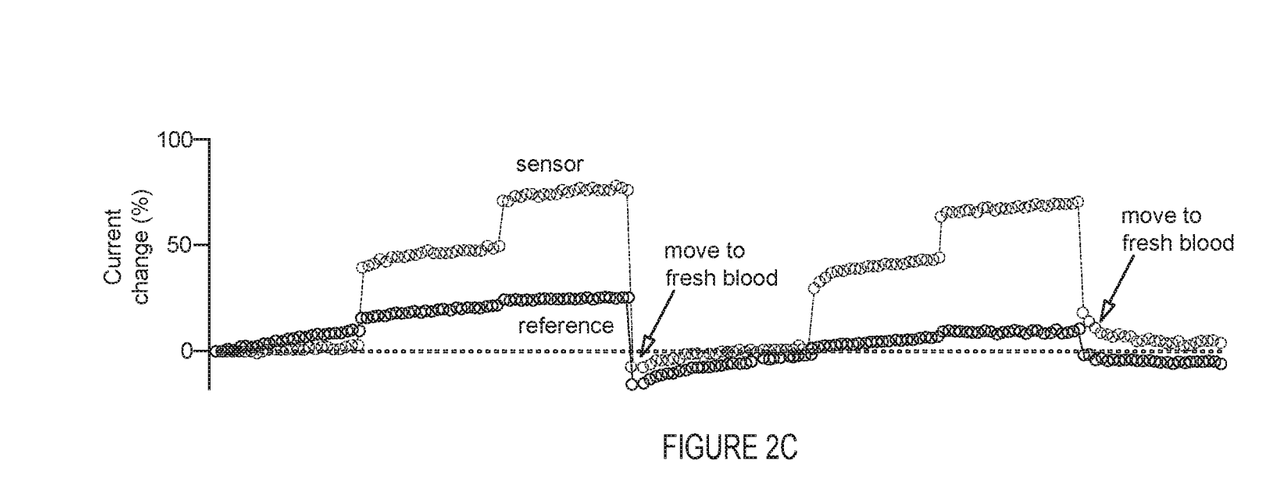
Figure 2D:
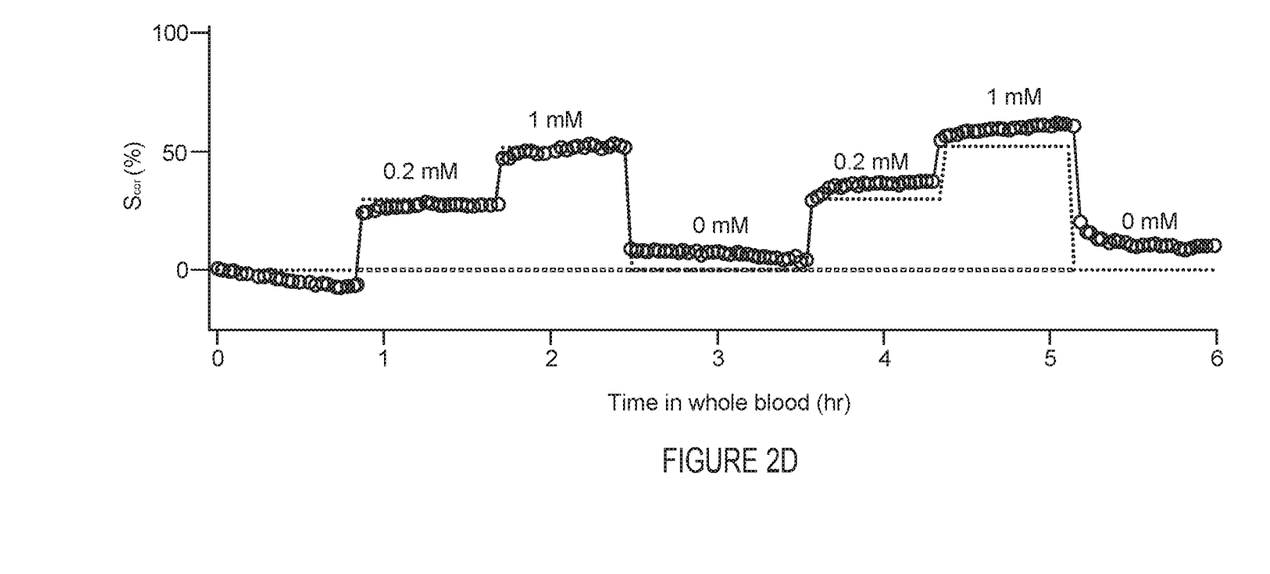

Dual-reporter baseline correction also corrected for sensor drift when the sensor was challenged with its specific molecular target. To demonstrate this, sensors were tested against varying pulses of cocaine in flowing whole blood over the course of several hours. Significant (~10% per hour), continuous drift was observed in both the MB and AQ currents in both the presence and absence of target (FIG. 2C). Application of the correction by Equation 2 nearly entirely eliminated this drift (Average signal of four sensors is depicted in FIG. 2D).

Figure 3A:
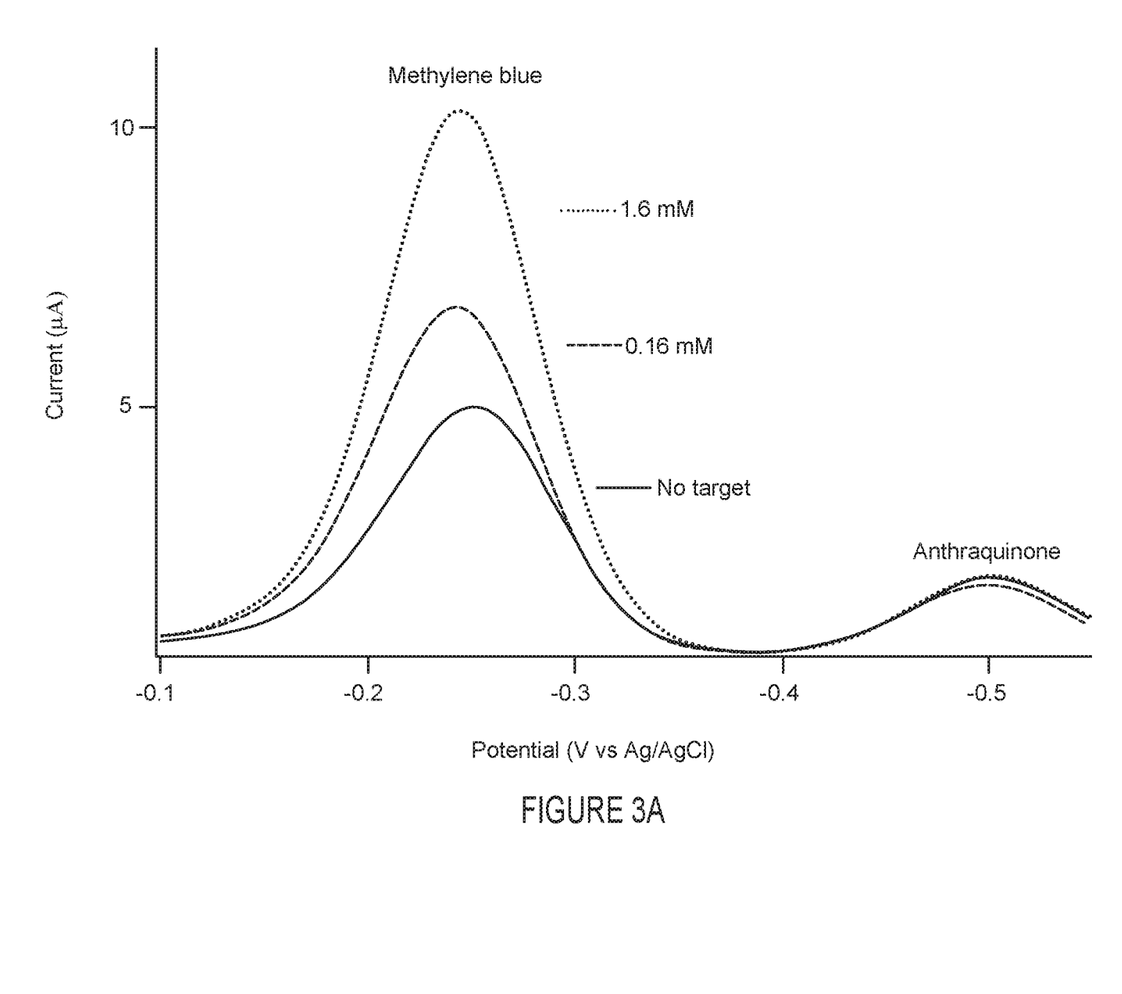
FIGS. 3A, 3B, 3C, and 3D depict average voltammograms for four dual-reporter kanamycin-detecting E-AB sensors.
Figure 3B:
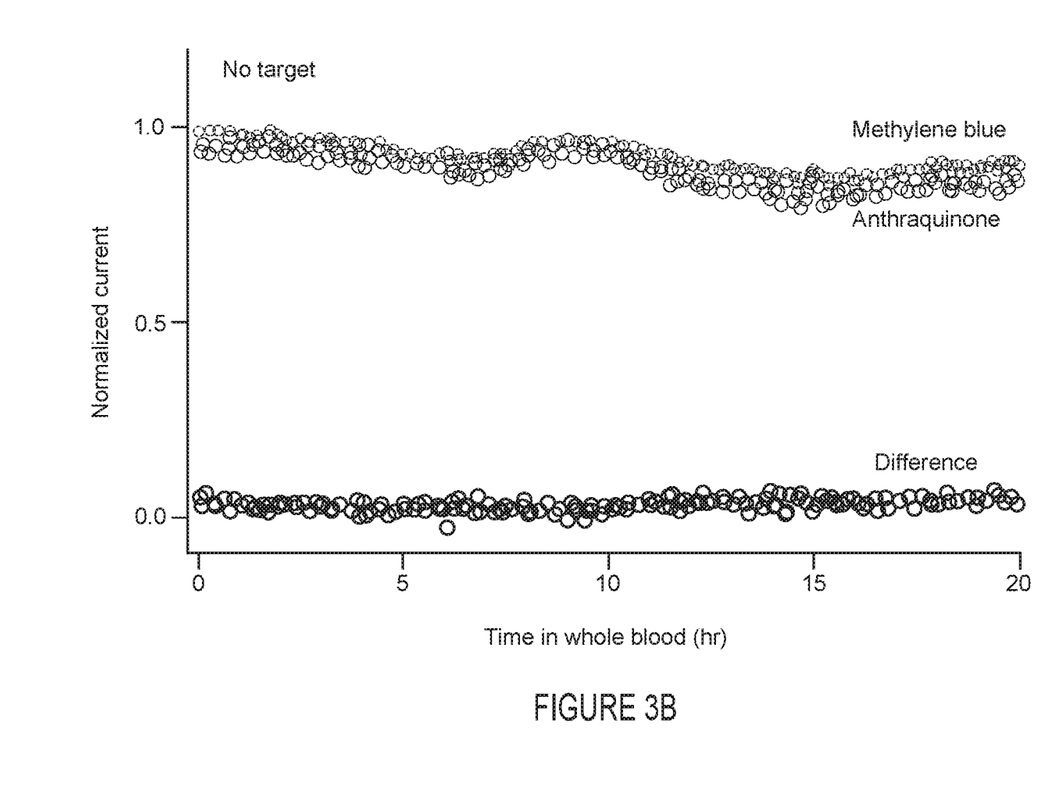
Figure 3C:
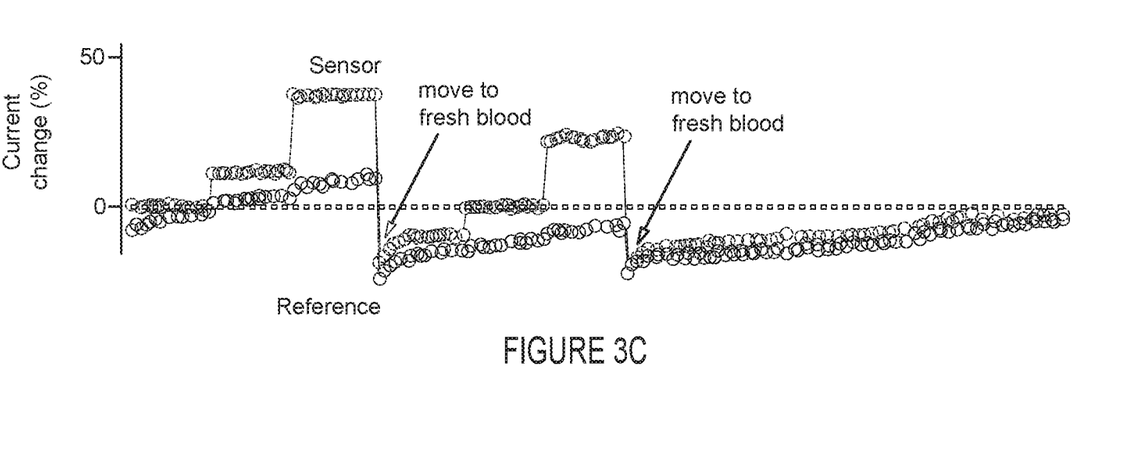
Figure 3D:
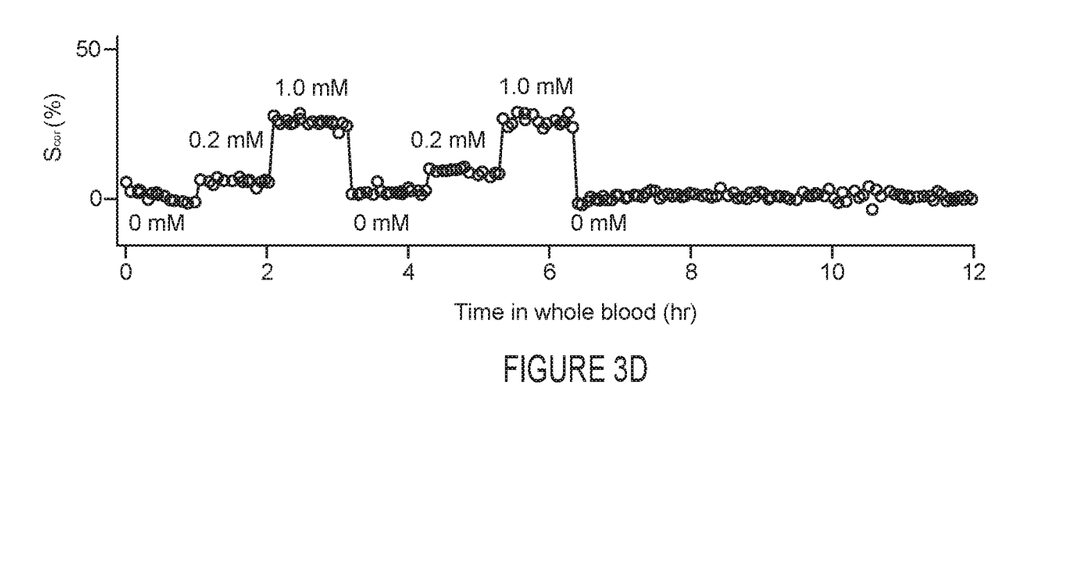

The dual-reporter approach to performing drift correction was also demonstrated for E-AB sensors employing other aptamers. A second set of sensors with a recognition element comprising an aptamer specific for the aminoglycoside antibiotics were fabricated. Clinical interest in the monitoring of these very narrow therapeutic index drugs is significant as they can cause hearing loss and kidney failure if administered inappropriately. Upon challenging a dual-reporter E-AB aminoglycoside sensor with kanamycin in whole blood, as expected, the current from an MB sensing reporter on the distal end of the aptamer increases significantly while that from an AQ reporter on its proximal end increases by less than 5% (FIG. 3A). Challenging these sensors in flowing whole blood for 20 hours, the currents from both reporters drifted by 15%-20% (FIG. 3B). Application of Equation 2 corrected for the drift, reducing the variability in signal to less than 2% over the same time period (FIG. 3B). Following this, the sensors were tested against varying pulses of kanamycin in flowing whole blood (FIG. 3C). Under these circumstances both currents drift by ~7% per hour in whole blood and also exhibits "jumps" of about 25% when removed from drug-containing whole blood and then returned to drug-free blood. Again, however, dual-reporter drift correction by Equation 4 reduced the background drift to less than 1% per hour and effectively eliminated the jumps seen upon transfer to fresh blood (FIG. 3D).

These results demonstrate a dual-reporter approach to performing baseline drift correction for E-AB sensors. The approach largely eliminated the drift seen when cocaine- and aminoglycoside-detecting E-AB sensors are deployed directly in flowing whole blood, reducing drift of order 20%~30% to less than 2% over many hours under challenging conditions and correcting both the steady drift seen in blood and the dramatic jumps in signal seen when the sensor is moved into fresh blood.

Materials and Methods. Gold wire (0.2 mm diameter) and tungsten wire (0.2 mm diameter) for electrode fabrication were used. Conductive silver epoxy adhesive materials were used fort the reference electrode. Teflon tubes were used as insulating materials. Gold wire electrodes were made as following procedures: the wire is composed of two parts: gold wire (5-6 mm, 0.2 mm diameter) and tungsten wire (8 cm, 0.2 mm diameter). These two components were first cold soldered by electrically conductive silver epoxy adhesive, and then tungsten wire and joint part were insulated by applying heat to shrinkable Teflon tubing around the body of the wires, leaving gold wire at one end exposed for DNA modification and 1 cm tungsten wire at the other end for the connections. After the insulation step, these wires were electrochemically roughened in order to increase the surface area. In specific, the sensors were immersed in 0.5 M sulfuric acid and pulsed between $E_{initial}$=0.0 V to $E_{high}$=2.0 V vs Ag/AgCl, back and forth, for 400,000 times. Each pulse had a duration of two milliseconds and no quiet time. All the probe oligonucleotides were dissolved with Tris buffer to a final concentration of 100 µM, aliquoted and stored at −20° C. ready for use. To fabricate sensors, the freshly cleaned electrodes were immersed in 200 nM DNA solution for 1 hour at room temperature, which was previously prepared by incubating a solution of 100 µM thiolated DNA and 20 mM TCEP (tris-(2-carboxyethyl) phosphine hydrochloride (1:200) for 1 hour at room temperature, and further diluted by PBS buffer (pH 7.0). The resulting sensors were washed with deionized water and then incubated in 20 mM 6-mercaptohexanol solution overnight at 4° C. The functionalized sensors were then rinsed with pure water prior to the measurements.

Electrochemical measurements. Electrochemical measurements were performed at room temperature using a potentiostat with and a standard three-electrode cell containing a platinum counter electrode and a Ag/AgCl reference electrode. Square wave voltammetry (SWV) was performed using a potential window −0.10 to −0.55 V (versus Ag/AgCl), a potential step of 0.001 V, an amplitude of 0.05 V at optimal frequency. The sensors were scanned quite frequently, and each SWV curve was recorded every 10 seconds. All the experiments were conducted in the electrochemical cell where the whole blood was continuously flowing in a closed-loop system at around 1 mL/s using a circulator pump to mimic circulation in the vasculature. After target response experiments the sensors were regenerated by washing with fresh, target-free blood (3×).

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:
1. A method of obtaining a drift-corrected normalized signal output from an electrochemical sensor, comprising
   by use of the electrochemical sensor, wherein the electrochemical sensor comprises a working electrode functionalized with a plurality of recognition elements wherein each recognition element is capable of selectively binding one or more target species, wherein each recognition element is functionalized with a sensing redox reporter, wherein binding of the one or more target species to each recognition element causes a detectable change in a charge transfer between the sensing redox reporter and the working electrode, wherein each recognition element is functionalized with a reference redox reporter, wherein binding of the one or more target species to each recognition element does not affect a charge transfer between the reference redox reporter and the working electrode;
   exposing the electrochemical sensor to a calibration sample of known target concentration and measuring both a sensing signal generated from the sensing redox reporter and a reference signal generated from the reference redox reporter;
   exposing the electrochemical sensor to a sample of unknown target concentration and measuring both a sensing signal generated from the sensing redox reporter and a reference signal generated from the reference redox reporter;
   calculating a normalized sensing signal, which is a ratio between the sensing signal measured in the sample of unknown target concentration and the sensing signal measured in the sample of known target concentration;
   calculating a normalized reference signal, which is a ratio between the reference signal measured in the sample of unknown target concentration and the reference signal measured in the sample of known concentration;

subtracting the normalized reference signal, which is indicative of drift, from the normalized sensing signal, which is indicative of both drift and target binding;

wherein the difference comprises a drift-corrected normalized signal responsive only to target induced binding.

2. The method of claim 1, wherein
the drift-corrected difference normalized signal is calculated as $$S_{cor} = \frac{i_S}{i_{S0}} - \frac{i_R}{i_{R0}}$$

wherein, $S_{cor}$ is the drift-corrected normalized signal, $i_S$ and $i_R$ are the sensing signal generated from the sensing redox reporter and the reference signal generated from the reference redox reporter in the sample of unknown target concentration, and $i_{S0}$ and $i_{R0}$ are the sensing signal generated from the sensing redox reporter and the reference signal generated from the redox reporter in the calibration sample of known target concentration.

3. The method of claim 1, comprising a further step of:
calculating a target concentration in the sample of unknown target concentration by applying a relationship between the target concentration and the normalized signal to the drift-corrected normalized signal responsive only to target induced binding.

4. The method of claim 1, wherein
each recognition element comprises an aptamer.

5. The method of claim 1, wherein
the one or more target species is selected from the group consisting of a small molecule drug, a metabolite, a hormone, a peptide, a protein, a carbohydrate, a nucleic acid, a lipid, a hormone, a metabolite, a growth factor, a neurotransmitter, a nutrient, a pollutant, a pathogen-induced or pathogen-derived factor, a pathogen, and a cell.

6. The method of claim 1, wherein
the calibration sample of known target concentration and the sample of unknown target concentration comprise a material selected from the group consisting of whole blood, serum, saliva, urine, sweat, interstitial fluid, spinal fluid, cerebral fluid, tissue exudates, macerated tissue samples, cell solutions, intracellular compartments, water, food, groundwater, biological sample, and environmental sample.

7. The method of claim 1, wherein
the electrochemical sensor is implanted in a body of a living organism.

8. The method of claim 1, wherein
the electrochemical sensor comprises a point-of-care system.

9. The method of claim 1, wherein
the electrochemical sensor comprises a sensor assembly configured as an in vivo sensor and further comprises, or is in connection with, electronic components for performing electrochemical measurements.

\* \* \* \* \*